US007632956B2

(12) United States Patent
Flachsmann et al.

(10) Patent No.: US 7,632,956 B2
(45) Date of Patent: Dec. 15, 2009

(54) FRAGRANCE INGREDIENTS, APPLICATIONS, COMPOSITIONS AND METHODS

(75) Inventors: Felix Flachsmann, Duebendorf (CH); Jean-Pierre Bachmann, Wädenswil (CH)

(73) Assignee: Givaudan SA, Vernier (CH)

( * ) Notice: Subject to any disclaimer, the term of this patent is extended or adjusted under 35 U.S.C. 154(b) by 93 days.

(21) Appl. No.: 11/577,173

(22) PCT Filed: Sep. 29, 2005

(86) PCT No.: PCT/CH2005/000562

§ 371 (c)(1), (2), (4) Date: Oct. 16, 2007

(87) PCT Pub. No.: WO2006/039822

PCT Pub. Date: Apr. 20, 2006

(65) Prior Publication Data

US 2009/0036690 A1 Feb. 5, 2009

(30) Foreign Application Priority Data

Oct. 14, 2004 (GB) ................................ 0423008.2

(51) Int. Cl.
*C07D 209/08* (2006.01)

(52) U.S. Cl. ...................................................... 548/510

(58) Field of Classification Search ................. 548/500, 548/510

See application file for complete search history.

(56) References Cited

U.S. PATENT DOCUMENTS

| | | | | |
|---|---|---|---|---|
| 4,598,156 | A * | 7/1986 | Martin | 548/501 |
| 6,566,533 | B1 * | 5/2003 | Barth et al. | 548/441 |
| 6,923,873 | B2 * | 8/2005 | Pageau et al. | 134/38 |

FOREIGN PATENT DOCUMENTS

| | | |
|---|---|---|
| DE | 10212687 A1 | 9/2002 |
| GB | 938903 | 10/1963 |

OTHER PUBLICATIONS

Shieh et al. (J. Org. Chem., 2003, 68(5); 1954-1957, published Feb. 7, 2003.*

* cited by examiner

*Primary Examiner*—Kamal A Saeed
*Assistant Examiner*—Valerie Rodriguez-Garcia
(74) *Attorney, Agent, or Firm*—Norris McLaughlin & Marcus, PA

(57) ABSTRACT

The use of indole carbamates as fragrance ingredients and fragrance applications comprising indole carbamates in an effective amount.

5 Claims, No Drawings

FRAGRANCE INGREDIENTS, APPLICATIONS, COMPOSITIONS AND METHODS

This is an application filed under 35 USC 371 of PCT/CH2005/000562.

This invention relates to compounds having anthranilate-like odour notes, their use as fragrance ingredients and to their use in fragrance compositions.

Compounds having anthranilate-like odour notes are well known. A prominent representative of this odour class is methyl anthranilate, which is widely used in commercial products. Unfortunately, methyl anthranilate leads to coloration under UV-irradiation. It also forms Schiff bases with aldehydes, which is not always desirable.

Surprisingly it has been found that certain indole carbamates constitute new powerful anthranilate-like odorants without having the disadvantages of the anthranilates known in the art. Furthermore, in comparison to anthranilates, certain indole carbamates of the present invention have better substantivity on a substrate, such as a fabric or hair, when used in an aqueous medium.

Accordingly the present invention refers in a first aspect to the use as a fragrance ingredient of a compound of formula I

I

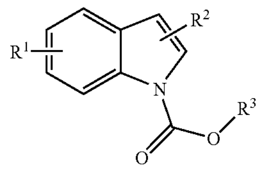

wherein $R^1$ is H; $C_{1-4}$ alkyl, such as methyl, ethyl, propyl, isopropyl or isobutyl; or $C_{2-4}$alkenyl, such as vinyl or isopropenyl;

$R^2$ is H or methyl;

$R^3$ is $C_{1-3}$ alkyl, such as methyl, ethyl, propyl, or isopropyl; allyl; or isopropenyl; and the total number of carbon atoms of a compound of formula I is 14 or less, preferably between 10 and 14, more preferably the number of carbon atoms is 10, 11, 12, 13 or 14.

Preferred are compounds of formula I wherein $R^1$ and $R^2$ are independently hydrogen or methyl, most preferred are compounds wherein $R^1$ is hydrogen or methyl and $R^2$ is hydrogen. Also preferred are compounds of formula I wherein $R^3$ is $C_{1-3}$ alkyl and $R^2$ is hydrogen.

The compounds of formula I may comprise one or more chiral centres and as such may exist as a mixture of stereoisomers, or they may be resolved in isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC or by stereoselective syntheses.

Particularly preferred are compounds of formula I selected from the group consisting of indole-1-carboxylic acid methyl ester, indole-1-carboxylic acid ethyl ester, indole-1-carboxylic acid isopropyl ester, indole-1-carboxylic acid allyl ester, 7-methyl-indole-1-carboxylic acid methyl ester and 5-methyl-indole-1-carboxylic acid methyl ester.

The compounds according to the present invention may be used alone or in combination with known odourant molecules selected from the extensive range of natural and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example, carrier materials, and other auxiliary agents commonly used in the art.

The following list comprises examples of known odourant molecules, which may be combined with the compounds of the present invention:

- ethereal oils and extracts, e.g. castoreum, costus root oil, geranium oil, jasmin absolute, patchouli oil, rose oil, sandalwood oil or ylang-ylang oil;
- alkohols, e.g. citronellol, Ebanol™, eugenol, geraniol, Super Muguet™, linalool, phenylethyl alcohol, Sandalore™, terpineol or Timberol™.
- aldehydes and ketones, e.g. α-amylcinnamaldehyd, Georgywood™, hydroxycitronellal, Iso E Super®, Isoraldeine®, Hedione®, maltol, methyl cedryl ketone, methylionone or vanillin;
- ether and acetals, e.g. Ambrox™, geranyl methyl ether, rose oxide or Spirambrene™.
- esters and lactones, e.g. benzyl acetate, cedryl actetate, γ-decalactone, Helvetolide®, γ-undecalactone or vetivenyl acetate.
- macrocycles, e.g. ambrettolide, ethylene brassylate or Exaltolide®.
- heterocycles, e.g. isobutylchinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odourant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in an alcoholic solution in amounts of from 0.1 to 20 weight percent, more preferably between 0.1 and 5 weight percent. However, these values are given only by way of example, since the experienced perfumer may also achieve effects or may create novel accords with lower or higher concentrations.

The compounds of the present invention may be employed into the fragrance application simply by directly mixing them or a fragrance composition comprising them with the fragrance application, or they may, in an earlier step be entrapped with an entrapment material such as for example polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation as a fragrance ingredient of at least one compound of formula I, wherein $R^1$, $R^2$ and $R^3$ have the same meaning as given above.

The compounds of the present invention may be prepared via reaction of an indole of formula II with a corresponding alkylchloroformate in the presence of a base, such as NaH, organic amine bases, metal alcoholates, e.g. KOtBu, NaOtBu, or other bases known to the person skilled in the art capable of neutralizing the hydrochloric acid formed during the reaction, as shown in scheme 1. The reaction is performed in an organic nonprotic solvent such as toluene, THF or acetonitrile or any other solvent suitable for acylation reactions. Preferably a polar co-solvent, such as N-methylpyrrolidone (NMP), DMPU or a similar co-solvent, which facilitates ionic reactions, is added to the reaction.

Scheme 1:

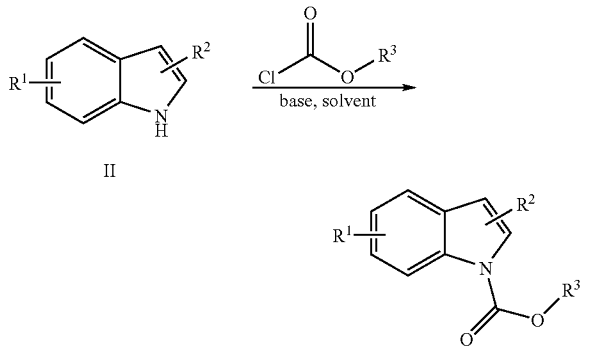

II

I

The invention is now further described with reference to the following non-limiting examples.

EXAMPLE 1

Indole-1-carboxylic acid methyl ester

Sodium hydride (5.23 g of a 55% suspension in mineral oil, 0.12 mol) is placed in a flask and the mineral oil is removed with hexane, then toluene (50 ml) is added. A solution of indole (11.7 g, 0.10 mol) in a mixture of toluene (30 ml) and N-methylpyrrolidone (40 ml) is added during 30 min. The resulting mixture is heated to 80° C. for 90 min, then cooled to room temperature and methylchloroformate (14.3 g, 0.15 mol) in toluene (30 ml) is added during 20 min, keeping the temperature between 10-20° C. by occasional cooling with an icebath.

The suspension is stirred for further 22 h at room temperature, diluted with MTBE and transferred to a separatory flask. The organic layer is washed with $H_2O$, 6 N HCl and brine, and then dried over $MgSO_4$. The crude is distilled at 0.05 mbar/85° C. to yield 11.8 g (67%) of product as a colourless oil, which is further purified by column chromatography on $SiO_2$ to yield 10.2 g (58%) of olfactorily pure indole-1-carboxylic acid methyl ester.

$^{13}$C-NMR: 151.4 (br. s), 135.2 (br. s), 130.5 (s), 125.5 (br. d), 124.5 (d), 123.0 (d), 121.0 (d), 115.1 (d), 108.1 (d), 53.8 (q). MS: 175 (90, $[M]^+$), 130 (100), 116 (56), 89 (56), 63 (31).

Odour description: orange, anthranilate, Yara Yara, ocimene.

EXAMPLE 2 TO 6

Further compounds as listed in Table 1 were prepared according to the procedure described in Example 1 above.

TABLE 1

| No | Structure | $^{13}$C-NMR (400 MHz, $CDCl_3$) | MS* | Odour description |
|---|---|---|---|---|
| 2 | 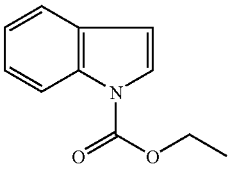 | 151.1 (br. s), 135.3 (br. s), 130.5 (s), 125.6 (br. d), 124.4 (d), 122.9 (d), 121.0 (d), 115.2 (d), 107.9 (d), 63.2 (t), 14.4 (q). | 189 (59, $[M]^+$), 161 (4), 144 (4), 130 (66), 117 (100), 89 (56). | floral, Ylang Ylang, blue grapes, orange blossom |
| 3 | 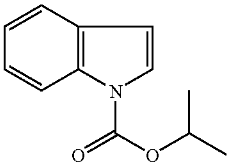 | 150.6 (br. s), 135.2 (br. s), 130.5 (s), 125.5 (br. d), 124.3 (d), 122.7 (d), 120.9 (d), 115.1 (d), 107.6 (d), 71.2 (d), 21.9 (q). | 203 (25, $[M]^+$), 161 (26), 144 (20), 117 (100), 89 (20). | floral, rosy, Yara Yara, powdery, orange blossom |
| 4 | 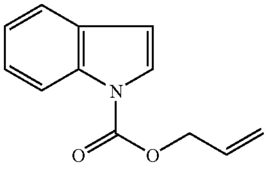 | 150.7 (br. s), 135.2 (br. s), 131.4 (d), 130.4 (s), 125.4 (br. d), 124.4 (d), 123.0 (d), 120.9 (d), 119.2 (t), 115.1 (d), 108.1 (d), 67.4 (t). | 201 (51, $[M]^+$), 156 (97), 130 (36), 116 (57), 89 (32), 41 (100). | fresh, marine, Anthranilate |

TABLE 1-continued

| No | Structure | $^{13}$C-NMR (400 MHz, $CDCL_3$) | MS* | Odour description |
|---|---|---|---|---|
| 5 | 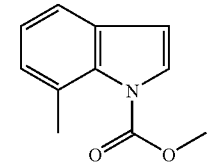 | 151.5 (s), 134.8 (s), 132.0 (s), 128.0 (d), 127.7 (d), 125.5 (s), 123.5 (d), 118.8 (d), 108.3 (d), 53.8 (q), 22.2 (q). | 189 (92, $[M]^+$), 144 (100), 130 (52), 103 (20), 77 (22). | Anthranilate, bitter orange, cresolic, animalic |
| 6 | 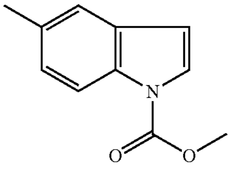 | 151.4 (br. s), 133.3 (br. s), 132.4 (s), 130.6 (s), 125.7 (d), 125.4 (br. d), 120.8 (d), 114.6 (d), 107.8 (d), 53.6 (q), 21.2 (q). | 189 (95, $[M]^+$), 144 (100), 130 (71), 103 (22), 77 (28), 59 (15). | Floral, Anthranilate |

*: molecular ion; in parentheses: 100% signal

EXAMPLE 7

Preparation of a Floral Perfume Composition

| | Weight parts |
|---|---|
| Benzyl Acetate | 35 |
| Phenylacetaldehyde | 12 |
| *Ambrettolide ® (oxacycloheptadec-10-en-2-one) | 50 |
| *Aurantiol Pur ® (methyl N-3,7-dimethyl-7-hydroxyoctylidenanthranilate) | 25 |
| *Bergamote Base | 100 |
| *Civette Base | 1 |
| Cyclohexal | 75 |
| α-Damascone | 2 |
| Dihydromyrcenol | 75 |
| Eugenol | 25 |
| Galaxolide ™ 50% in Diethylphtalate | 200 |
| Geranium Essence | 15 |
| Heliotropine | 25 |
| Hydroxycitronellal | 30 |
| Lilial ® (p-tert.Butyl-alpha-methyldihydrocinnamic aldehyde) | 200 |
| Methyl Cedryl Ketone | 85 |
| Ylang Ylang Essence | 20 |
| Total | 975 |

*Commercially available at Givaudan SA, Vernier, Switzerland.

Addition of 25 weight parts of indole-1-carboxylic acid methyl ester of Example 1 to this composition imparts a sweet natural orange blossom note to the perfume and enhances the overall floral aspect of middle notes and dryout.

The invention claimed is:

1. A fragrance composition comprising a compound of formula I

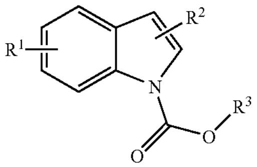

I wherein $R^1$ is H, $C_{1-4}$ alkyl, or $C_{2-4}$ alkenyl;

$R^2$ is H or methyl; and $R^3$ is $C_{1-3}$ alkyl, allyl, or isopropenyl;

the total number of carbon atoms of a compound of formula I is 14 or less; and at least one other odourant molecule.

2. A fragrance composition according to claim 1, comprising as compound I, a compound selected from the group consisting of: indole-1-carboxylic acid methyl ester, indole-1-carboxylic acid ethyl ester, indole-1-carboxylic acid isopropyl ester, indole-1-carboxylic acid allyl ester, 7-methyl-indole-1-carboxylic acid methyl ester and 5-methyl-indole-1-carboxylic acid methyl ester.

3. A method of manufacturing a fragrance application, comprising: adding a fragrance composition according to claim 1, to said fragrance application.

4. A method according to claim 3, wherein the fragrance application is selected from the group consisting of: perfume, household product, laundry product, body care product and cosmetics.

5. A fragrance composition comprising a compound of formula I

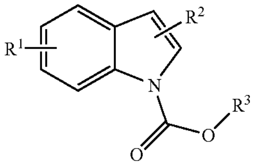

I wherein $R^1$ is H, $C_{1-4}$ alkyl, or $C_{2-4}$ alkenyl;

$R^2$ is H or methyl; and $R^3$ is $C_{1-3}$ alkyl, allyl, or isopropenyl; and the total number of carbon atoms of a compound of formula I is 14 or less, and further wherein the compound of formula I provides an anthranilate-like odour note to the fragrance composition.

* * * * *